(12) United States Patent
Jaspers et al.

(10) Patent No.: US 9,775,641 B2
(45) Date of Patent: Oct. 3, 2017

(54) HOLDING DEVICE FOR HOLDING A MANUALLY OPERATED MEDICAL DEVICE

(75) Inventors: Joris Emanuel Nicolaas Jaspers, Bodegraven (NL); Jesse Mattan Bosma, Utrecht (NL)

(73) Assignee: UMC Utrecht Holding B.V., Utrecht (NL)

(*) Notice: Subject to any disclaimer, the term of this patent is extended or adjusted under 35 U.S.C. 154(b) by 886 days.

(21) Appl. No.: 13/500,170

(22) PCT Filed: Oct. 7, 2009

(86) PCT No.: PCT/NL2009/050606
§ 371 (c)(1),
(2), (4) Date: Jun. 5, 2012

(87) PCT Pub. No.: WO2011/043644
PCT Pub. Date: Apr. 14, 2011

(65) Prior Publication Data
US 2012/0296281 A1    Nov. 22, 2012

(51) Int. Cl.
*A61B 1/32* (2006.01)
*A61B 17/34* (2006.01)
(Continued)

(52) U.S. Cl.
CPC .......... *A61B 17/3421* (2013.01); *A61B 90/50* (2016.02); *A61B 34/70* (2016.02); *A61B 2017/347* (2013.01)

(58) Field of Classification Search
CPC ................ A61B 17/02; A61B 17/0293; A61B 2017/348; A61B 19/26; A61B 17/3421; A61B 2017/347; A61B 17/3423
(Continued)

(56) References Cited

U.S. PATENT DOCUMENTS 5,441,042 A * 8/1995 Putman .................... 600/102
5,888,190 A * 3/1999 Meyer .................. F16M 11/04
                                                           248/278.1
(Continued)

FOREIGN PATENT DOCUMENTS

EP          1647237       4/2006
JP         2011155880     6/1999
JP         2000510716     8/2000

*Primary Examiner* — Si Ming Ku
(74) *Attorney, Agent, or Firm* — Edward J. Baba; Khin K. Chin; Bozicevic, Field & Francis LLP

(57) ABSTRACT

Holding device for holding a manually operated medical device in place, comprising: a connector arranged to connect the holding device to a positioning apparatus; a clamp member arranged to clamp the medical device, wherein the clamp member is moveable between a locking position wherein the medical device is clamped and a moving position wherein the medical device is moveable with respect to the holding device; a joint assembly arranged to allow movement between the clamp member and the connector, wherein the joint assembly is moveable between a moving position wherein the clamp member is moveable with respect to the connector and a locking position wherein movement between the clamp member and the connector is prevented, and; an actuator for moving both the joint assembly and the clamp member between the moving positions and the locking positions.

18 Claims, 5 Drawing Sheets

Figure 7A:
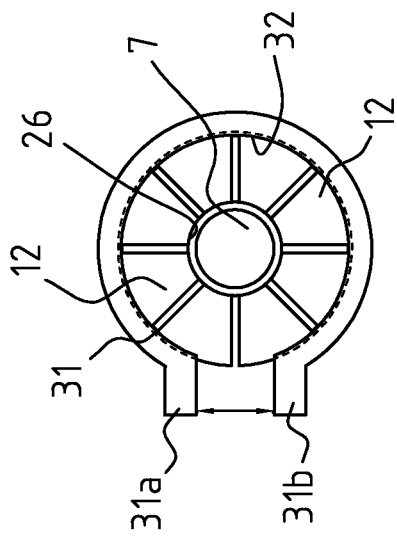

(51) Int. Cl.
*A61B 90/50* (2016.01)
*A61B 34/00* (2016.01)

(58) Field of Classification Search
USPC .................................................. 600/201–249
See application file for complete search history.

(56) References Cited

U.S. PATENT DOCUMENTS

| | | |
|---|---|---|
| 2003/0086749 A1 | 5/2003 | Oliver et al. |
| 2003/0199738 A1 | 10/2003 | Yager |
| 2004/0176763 A1* | 9/2004 | Foley ................ A61B 17/3421 606/60 |
| 2007/0250112 A1* | 10/2007 | Ravikumar et al. .......... 606/205 |
| 2010/0010446 A1* | 1/2010 | Schweitzer ........ A61B 17/3498 604/167.01 |

* cited by examiner

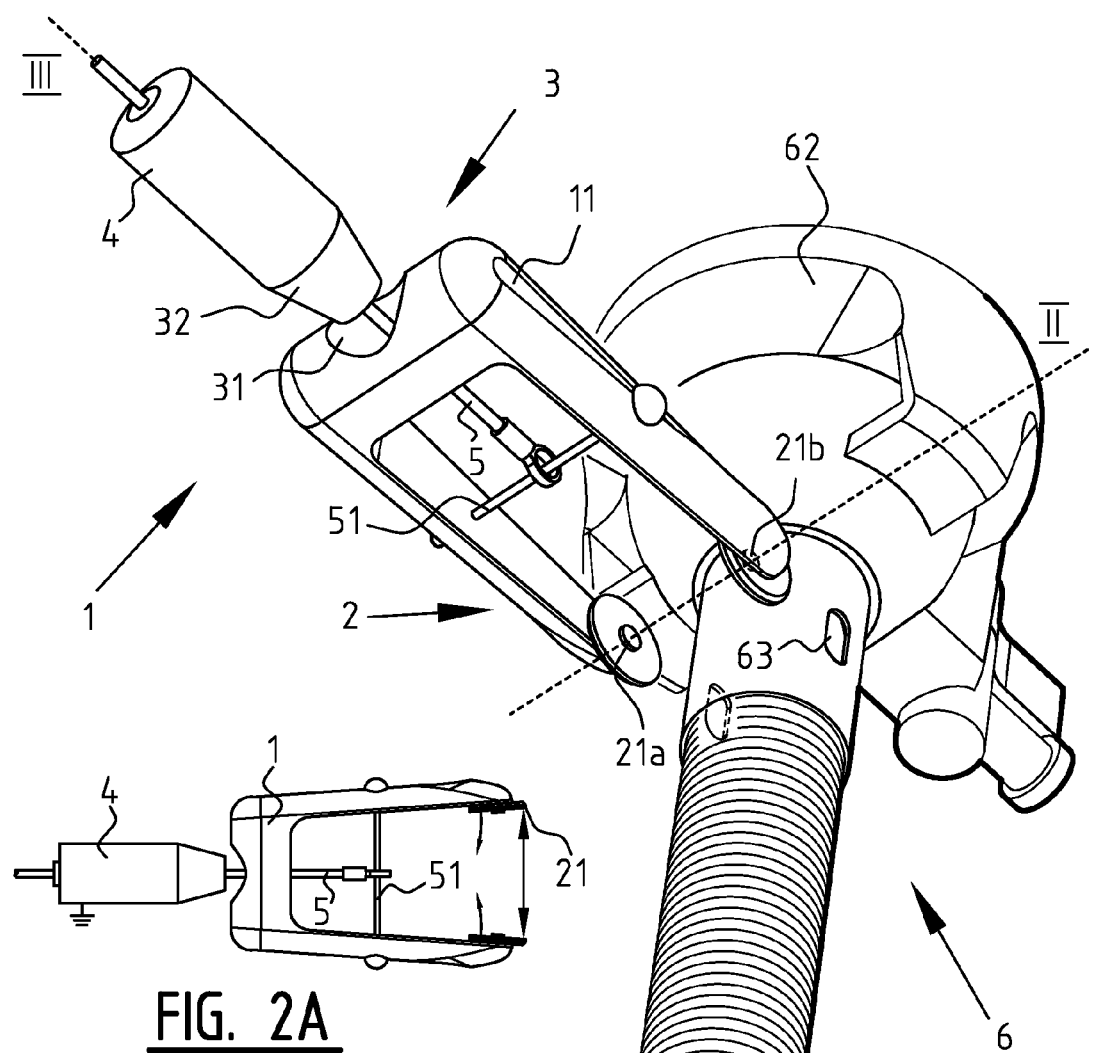
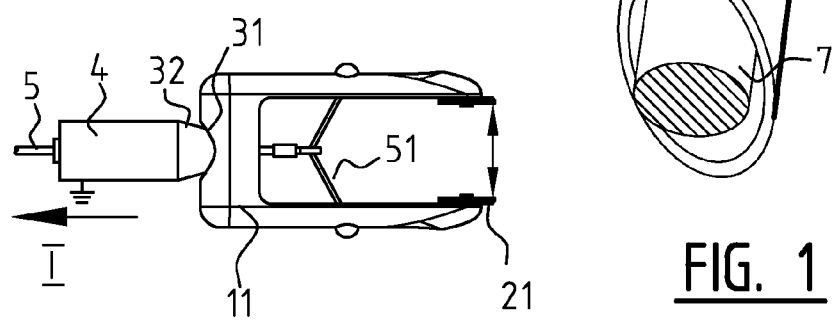

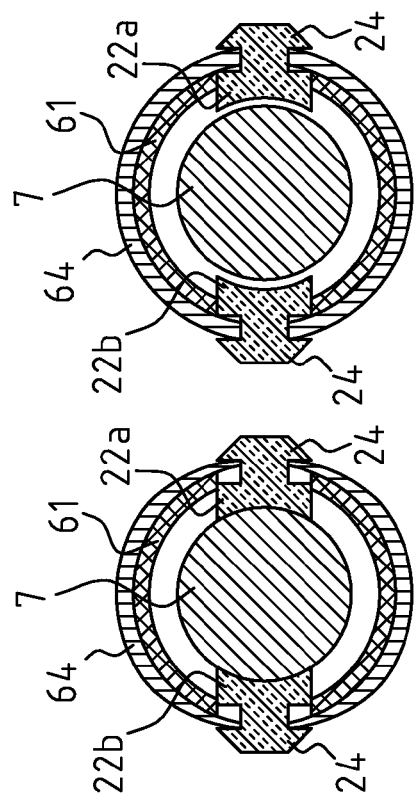
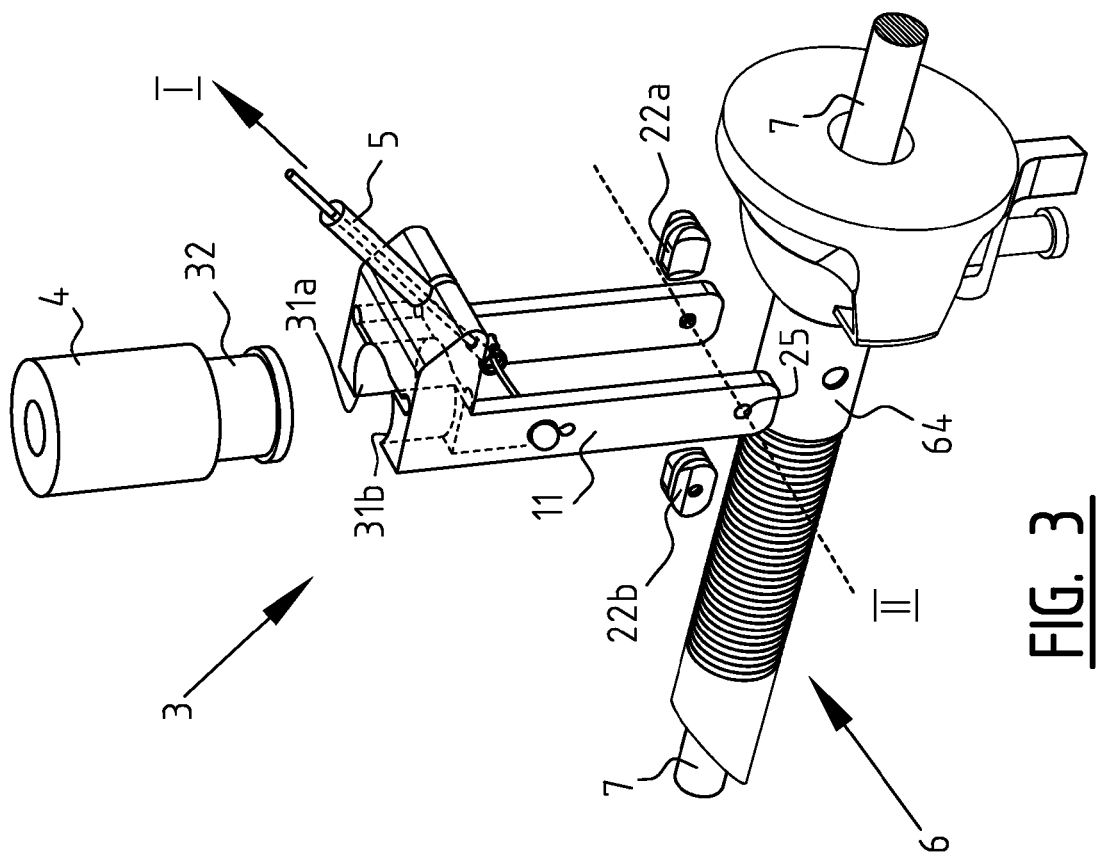

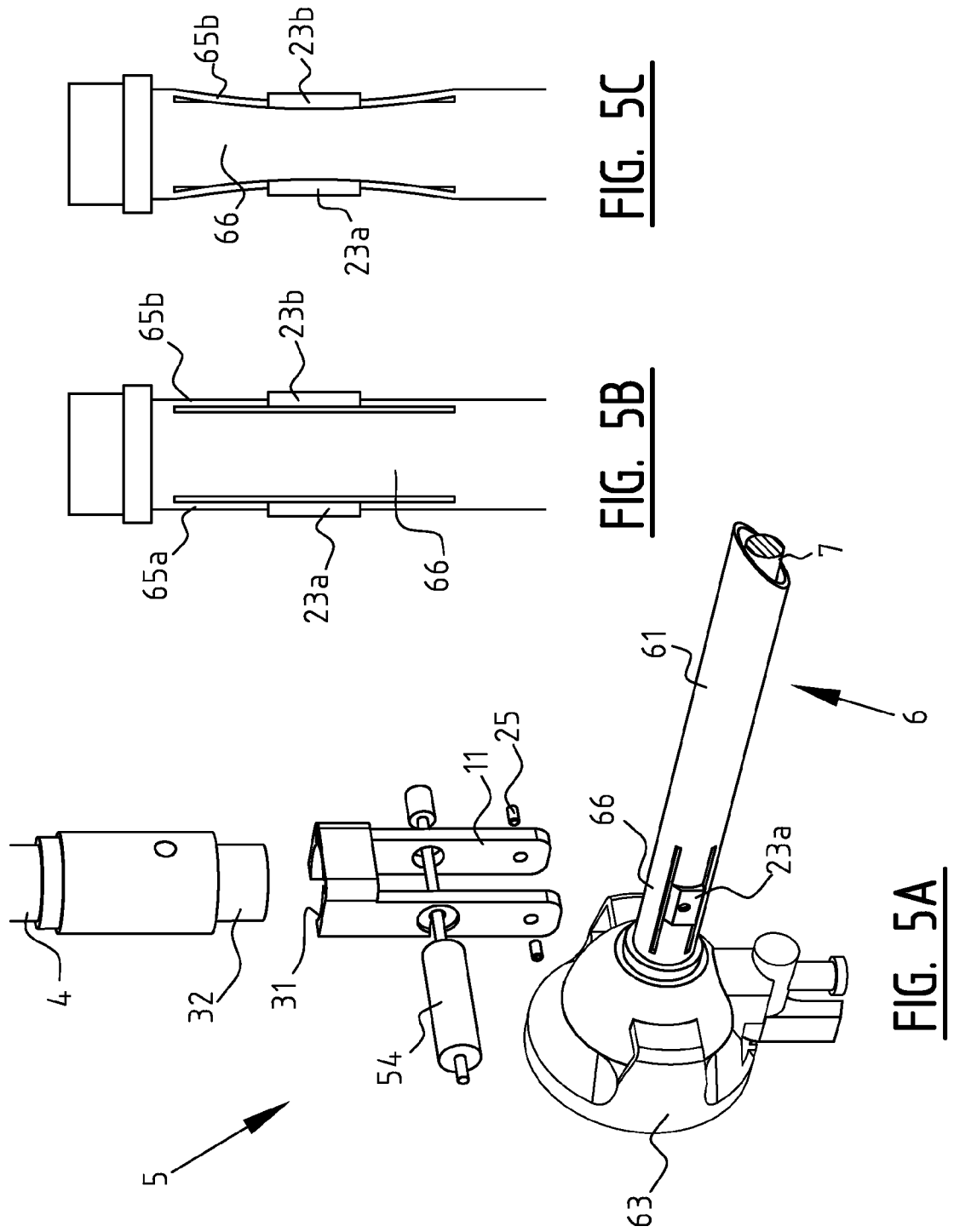

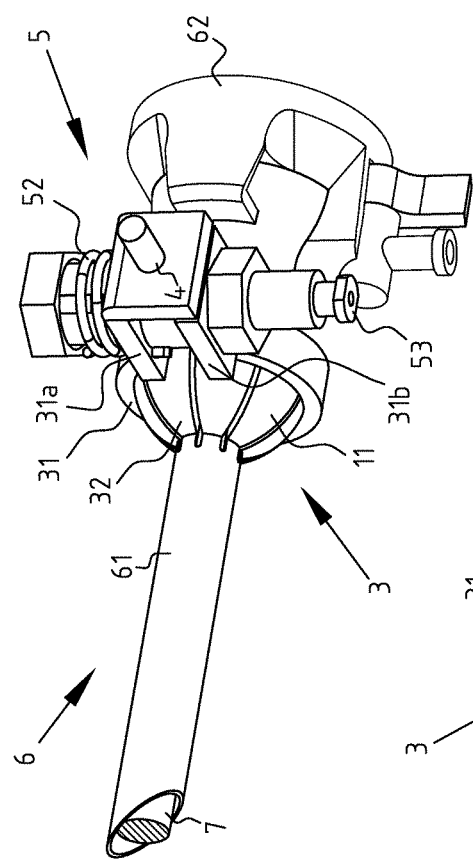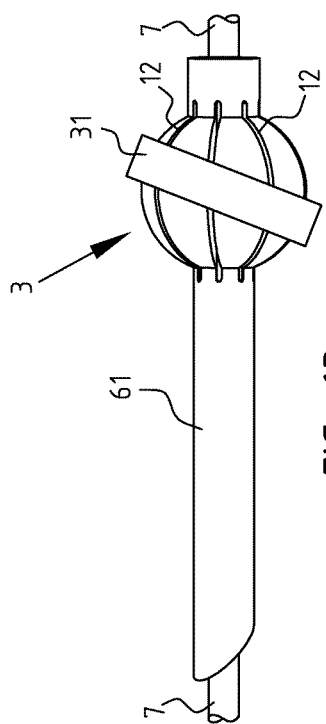

HOLDING DEVICE FOR HOLDING A MANUALLY OPERATED MEDICAL DEVICE

The present invention relates to a holding device for holding a manually operated medical device in place. The invention furthermore relates to a guiding tube for use with a holding device.

In minimally invasive or laparoscopic surgery, operations in the abdomen are performed through small incisions (usually 0.5-1.5 cm) as compared to larger incisions needed in traditional surgical procedures. Through these incisions, the surgeon carries out the operation using a plurality of medical instruments such as a scope, a retractor, a suction device and cutting devices.

It is however a problem that a surgeon is not able to control more than two laparoscopic instruments, therefore he depends on one or more assistants to control the other instruments. This results in a number of drawbacks, including the need for three or more persons in the sterile field, wherein one assistant is performing a rather static task of holding instruments. Further, the surgeon has no direct control over his viewing direction when an assistant holds the scope, which leads to communication problems and disturbs the surgeon's eye-hand co-ordination. Furthermore, the laparoscopic image from a scope is often unstable, due to tremors and sudden movements of the surgical assistant.

It is known to provide a positioning apparatus for holding the medical device. The positioning apparatus can be in the form of a plurality of arms interconnected by mechanical linkages. The positioning apparatus can be locked in a locking position, for instance by freezing the linkages, for holding the medical device stable. When the medical device needs to be moved, the positioning apparatus is moved to a moving position by allowing movement between the arms.

Although the medical device can be held stable by said positioning apparatus, moving the medical device using said positioning apparatus is considered hard by the surgeons.

It is therefore goal of the present invention, amongst other goals, to provide an efficient, intuitive and/or easy to use holding device for holding a manually operated medical device.

The above goal is met by the present invention, amongst other goals, by a holding device as defined in the appended claim 1.

Specifically, the above goal, amongst other goals, is met by the present invention by a holding device for holding a manually operated medical device in place, comprising:
  a connector arranged to connect the holding device to a positioning apparatus;
  a clamp member arranged to clamp the medical device, wherein the clamp member is moveable between a locking position wherein the medical device is clamped and a moving position wherein the medical device is moveable with respect to the holding device;
  a joint assembly arranged to allow movement between the clamp member and the connector, wherein the joint assembly is moveable between a moving position wherein the clamp member is moveable with respect to the connector and a locking position wherein movement between the clamp member and the connector is prevented, and;
  an actuator for moving both the joint assembly and the clamp member between the moving positions and the locking positions.

With the holding device according to the invention, the surgeon can move the medical device with respect to the positioning apparatus with a single manipulation of the actuator, instead of using two hands as is common in the art. Preferably a single actuator is arranged to move both the joint assembly and the clamp member between the moving and the locking positions, more preferably synchronously.

The clamp member in the moving position allows movement of the medical device in at least one degree of freedom, whereby the joint assembly allows movement in at least one further degree of freedom. By using the actuator, both the clamp member and the joint assembly can be moved to the moving position, allowing movement of the medical device in the at least two degrees of freedom.

Preferably, the clamp member is arranged to limit and allow movement of the medical device in at least the longitudinal direction of the medical device. This for instance allows the depth of the device in the patient to be altered. The joint member is preferably arranged to limit and allow rotation of the medical device on at least one rotation axis, preferably on two or more preferably on three axes of rotation. This gives the surgeon the freedom to displace the medical device in the patient.

According to a preferred embodiment of the holding device according to the invention, at least one of the clamp member and the joint assembly is arranged to move between the positions due to movement of the other one of the joint assembly and the clamp member between the positions. When the actuator for instance moves the joint assembly from the locking to the moving position, the clamp member is also moved from the locking position to the moving position. Preferably, one of the clamp member and the joint assembly is arranged to move the other one of the joint assembly and the clamp member. The clamp member is then for instance moved between the positions by the actuator, while the clamp member then moves the joint assembly between the positions. The clamp member, the joint assembly and the actuator are hereby connected in series, wherein movement of the actuator results in movement of both the joint assembly and the clamp member.

According to a further preferred embodiment of the holding device according to the invention, the clamp member and at least one part of the joint assembly are formed integrally in a holding body, wherein the actuator is arranged to move the holding body between a moving and a locking position for moving the clamp member and the joint assembly between the moving and the locking positions. Providing the clamp member and one part of the joint member on a single holding body allows the movement of both the clamp member and the joint member between the positions by moving said holding body.

Preferably the holding body is at least partially manufactured from a resilient material, wherein the holding body is preferably pre-stressed towards the moving or the locking position of the holding body. The actuator is hereby arranged to move the holding body towards a first position, wherein the moving body moves towards the second position due to the resilient material. This allows the use of an actuator having a single working direction. Preferably, the holding body is pre-stressed towards the locking position. This increases the safety of the device and prevents unintentional movement of the medical device due to for instance failure of the actuator.

It should be noted that a material can be resilient due to its mechanical properties, i.e. its Young's modulus, but it is for instance also possible to provide the holding body with weakenings or other structural features for increasing the resilient properties of the holding body.

According to a further preferred embodiment, the actuator is chosen from the group of a hydraulic, a pneumatic, electrical or a mechanical actuator. Suitable mechanical actuators comprise for instance a nut or a Bowden cable. Other actuators may however also be used.

According to a further preferred embodiment, the actuator comprises a manipulator allowing the surgeon to operate the actuator, wherein the manipulator extends at a distance from the actuator, in particular at a distance from the holding device. This allows the actuator to be operated from a distance. Preferably the manipulator extends on the device to be held in place. This allows the surgeon to move the holding device between the moving and the locking position without letting go the medical device. Between the actuator and the manipulator suitable connection means can be provided, for instance in the form of a pneumatic or hydraulic conduit, an electrical wire or a Bowden cable. The manipulator may for instance be in the form of a knob, a switch, a handle or a combination thereof.

Preferably the actuator comprises biasing means, for instance in the form of a spring. When the actuator is operated, the holding device is moved between the positions and when the actuator stops operating, the biasing means urge the holding device to the initial position.

According to a further preferred embodiment, the joint assembly comprises a protruding member and a receiving member for receiving the protruding member, wherein the receiving member is substantially complementary to the protruding member, wherein the actuator is arranged to induce movement between the receiving member and the protruding member for moving between the locking and the moving position. In the locking position, the protruding member engages the receiving member such that friction between the members prevents movement between said members. By inducing movement and changing the distance between the members, the friction decreases, allowing movement between the members.

Preferably the protruding member has a substantially cylindrical, conical or spherical shape. Dependent on the desired number of degrees of freedom, a suitable protruding member can be used. A cylindrical and a conical member for instance allow rotation along on the longitudinal axis of the cylinder or cone, whereas a spherical member allows free rotation between the protruding member and the receiving member.

According to a further preferred embodiment of the holding device according to the invention, the holding body comprises a channel for receiving the medical device, wherein an inner surface of said channel forms said clamp member, wherein an outer surface of the holding body forms the protruding member of the joint assembly, and wherein the actuator is arranged to deform the holding body for moving the holding body between the moving and the locking positions. By deforming the holding body, both the clamping member and the joint assembly are moved between the positions.

In this embodiment, an outer surface, preferably substantially the whole outer surface, of the holding body forms the protruding member. The holding body is held in the receiving member, which is substantially complementarily to the outer surface of the holding body.

A channel arranged in the holding body is hereby arranged to hold the medical device. Preferably the channel is open on both sides of the channel. This increases the degree of movement of the medical device with respect to the holding body. When the holding body is deformed, the inner surface or wall of the channel will engage the medical device, hereby clamping said device. The clamping member in the form of the inner surface preferably moves radially inwards with respect to the longitudinal axis of the channel, resulting in said clamping action.

Preferably the holding body comprises a plurality of segments extending radially from said channel. This allows an efficient deformable holding device, whereby relative movement of the segments allow the deformation resulting in the movement between the positions.

According to a further preferred embodiment of the holding device according to the invention, the actuator is arranged to modify the diameter of the receiving member of the joint assembly for deforming the holding body for moving both the joint assembly and the clamp member between the locking positions and the moving positions. The diameter of the receiving member can for instance be decreased, thereby deforming the holding body. The friction between the receiving member and the outer surface of the holding member will therefore increase, preventing movement between the receiving member and the holding body. Further, the inner surface of the channel will clamp the medical device due to this deformation. In this case, both the protruding part, formed by the outer surface of the holding body, and the clamp member, formed by the inner surface of the channel, will move radially inwards with respect to the longitudinal axis of the medical device when moving to the locking position.

It is however also possible to deform the holding body by increasing its volume, for instance using hydraulics or pneumatics. Due to this increasing volume, the inner surface of the channel will be urged towards the medical device and the outer surface will be urged towards the receiving member. In this case, the clamp member moves radially inwards, while the outer surface moves radially outwards.

According to a further preferred embodiment of the holding device according to the invention, the holding body is formed integrally with a guiding tube, in particular a trocar, wherein the clamping member forms an inner wall of said guiding tube. The channel of the holding body preferably forms an inner wall of the guiding tube. Forming the holding device, more in particular the holding body, integrally with a guiding tube results in a holding device having a rotation point of the medical device close to the incision in the patient. This increases the reach of the medical device in the patient. Preferably, the holding device is furthermore provided with a seal for making the guiding tube airtight. The seal can comprise a coating, for instance in the form of silicones.

According to another preferred embodiment of the holding device according to the invention, the holding body is substantially U-shaped, wherein the two legs of said U-shaped holding body form the clamp members for clamping the medical device there between. By moving the legs towards or away from each other using the actuator, the clamp member can be moved between the locking and the moving position.

Preferably the clamp members comprise clamping shoes, wherein the clamping shoes are arranged to clamp the medical device in the locking position around a part of the perimeter of said medical device. The clamping shoes preferably comprise a clamping surface complementarily to the medical device, enhancing the clamping action. The clamping shoes can be detachably connected to the holding body, allowing replacement of the shoes or adjustment of the holding device for use with a particular medical device.

More preferably the clamping member, in particular a clamping shoe, is provided moveable on the holding body, in particular rotatable. This allows rotation of the medical device with respect to the legs in the moving position. The connection between the clamping member and the holding body hereby comprises a further joint assembly. The joint assembly can hereby be provided with a protruding and a receiving part as discussed before. In this case, when the clamp member is moved to the locking position, also the joint assembly between the clamp member and the holding body is moved to the locking position due to the clamping action.

According to a further preferred embodiment, the part of the joint assembly extends in the base of the U-shaped holding body. This results in a compact composition and allows the use of a single actuator to move both the joint assembly and the clamp member between the positions.

According to a further preferred embodiment, the receiving member of the joint assembly is provided on the holding body, wherein the actuator is arranged to modify the shape of the receiving member. By deforming the holding body, the shape of the receiving member is changed, hereby changing the degree of engagement between the protruding member and the receiving member for movement between the positions. The change of shape of the receiving member can for instance comprise a change in diameter of the receiving member or a change in distance between two surfaces of the receiving member.

According to a further preferred embodiment, the actuator is arranged to translate the receiving member and the protruding member of the joint assembly for moving said member between the moving and the locking position. By moving the protruding member with respect to the receiving member, the degree of engagement and thereby the friction between the members is altered, thereby moving the joint assembly between the positions. Preferably the protruding member comprises a conical shape, allowing a firm clamping action in the locking position.

It should be noted that it is possible to provide a plurality of joint assemblies, for instance between the holding body and the connector and between the holding body and the clamping member. According to the invention, the actuator is arranged to move both the clamping member and the joint assemblies between the positions.

According to a further preferred embodiment of the holding device according to the invention, the clamp member is arranged to clamp the medical device in a guiding tube, in particular a trocar, adapted for use with the holding device. Holding the medical device through the guiding tube results in a rotation point of the medical device close to the incision in the patient. This increases the reach of the medical device in the patient. The guiding tube is preferably provided with openings for receiving the clamp member, in particular the clamping shoes. The guiding tube can furthermore be provided with a seal for making the guiding tube-holding device combination airtight. Preferably the seal comprises a resilient tube extending coaxially with respect to the guiding tube. The seal is more preferably arranged to hold the clamp member, more preferably the clamping shoes. The clamping shoes may be provided with a groove for receiving the seal, wherein the seal is provided with openings for receiving said shoes. This allows the clamp member to be connected to the guiding tube for further connection with the holding body.

Preferably the clamp member is formed integrally with the guiding tube, wherein the inner wall of said guiding tube is moveable for clamping said medical device. The clamp member, for instance in the form of clamping shoes, can then be connected to the holding body using suitable connection means, for instance in the form of joint assemblies as discussed above.

The invention furthermore relates to a guiding tube, in particular a trocar, for use with the holding device according the invention, wherein a part of the wall of the tube is arranged to receive the clamp member. The wall can for instance be provided with an opening, preferably two openings, for receiving the clamp member. It is however also possible that the tube is provided with a moveable wall for cooperation with the clamp member, or provided with an integral clamp member as discussed above. The guiding tube can then easily be connected to a holding device according to the invention.

It should further be noted that the invention is not limited to a conventional trocar. It may for instance be possible to use the holding device according to the invention with a guiding tube provided with a plurality of entries in the patient. Holding a medical device in place in one entry with the holding device according to the invention then results in a stable positioning of said guiding tube.

The invention furthermore relates to a method for holding a manually operated medical device in place using a holding device according to the invention.

Figure 7B:
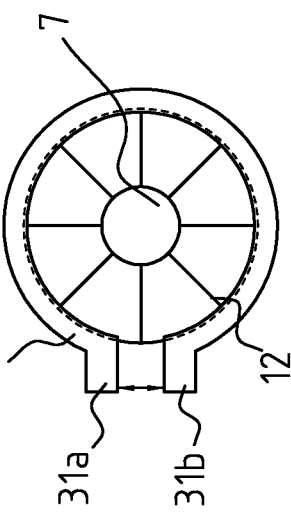
Figure 8A:
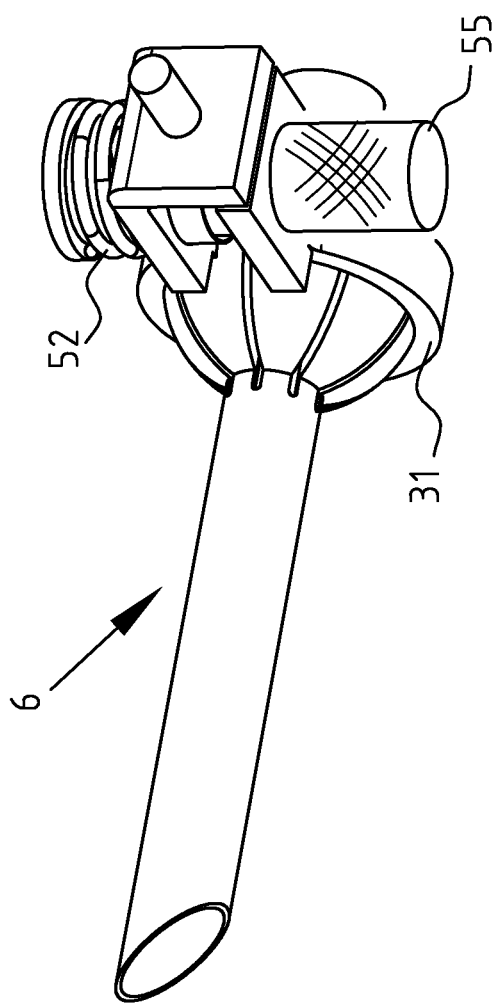

The present invention is further illustrated by the following Figures, which show a preferred embodiment of the device according to the invention, and are not intended to limit the scope of the invention in any way, wherein:

FIG. 1 schematically shows a first embodiment of the holding device;

FIGS. 2a and 2b schematically show the device of FIG. 1 in the moving and locking position, respectively;

FIG. 3 schematically shows an alternative of the device of FIG. 1;

FIGS. 4a and 4b schematically show the clamping action of the device of FIG. 3 in cross-section;

FIG. 5a schematically shows a further alternative of the device;

FIGS. 5b and 5c schematically show the clamping action of the device of FIG. 5a in cross-section;

FIG. 6a schematically shows a second embodiment of the holding device;

FIG. 6b schematically shows the holding device of FIG. 6a in side-view;

FIGS. 7a and 7b schematically show the clamping action of the device of FIG. 6a in cross-section, and;

FIGS. 8a en 8b schematically show alternatives of the device of FIG. 6a.

In FIG. 1 a holding device in the form of a clamp is shown. The clamp 1 is provided with a connector 4 which is connected to a positioning apparatus (not shown). Such an apparatus can for instance be in the form of a plurality of mutual moveable arms. The positioning apparatus provides a stable position for the connector 4. The clamp 1 is arranged to clamp a laparoscopic instrument 7 in a locking position. In a moving position of the clamp 1, the instrument is allowed to move with respect to the connector 4.

A laparoscopic instrument 7 is normally inserted into the patient using a guiding tube in the form of a trocar 6. The trocar 6 is provided with an inlet part 62 and a tube part 61. The tube 61 is according to the invention provided with openings 63 which allow the clamp 1 to clamp the instrument held in said trocar 6.

The clamp 1 comprises a holding body in the form of a U-shaped body 11. The legs of the U-shaped member 11 are provided with a clamp member 2 in the form of clamping shoes 21a and 21b. The clamping shoes 21a and 21b cooperate with openings 63 to engage the instrument 7 held in the tube 61.

In the moving position, the trocar 6 holding the instrument 7 is allowed to rotate with respect to the clamping shoes 21a 21b on axis II. In the locking position, next to preventing movement of the instrument in its longitudinal direction, also rotation on axis II is prevented due to the clamping action of the shoes 21a and 21b on the instrument 7 as will be explained more in detail below.

The U-shaped body 11 is furthermore provided with a joint assembly 3 formed by a protruding member in the form of a cone 32 which can be received in a receiving member in the form of opening 31. The opening 31 is also shaped conical, allowing a tight fit of the cone 32 and the opening 31 in the locking position.

For moving the clamp 1 between a locking position and a moving position, an actuator in the form of a Bowden cable 5 is provided. The cable 5 is connected to a connecting wire 51 which interconnects the legs of the U-shaped body 11. The cable 5 extends through the opening 31 and is held coaxially in the connector 4.

In FIG. 2a the clamp 1 is shown in its moving position. The distance between the clamping shoes 21 is hereby larger than the distance in the locking position as shown in FIG. 2b. In the moving position, the shoes 21 allow movement of the instrument with respect to the clamping shoes 21 in a longitudinal direction of the trocar 6. Further, the instrument 7 is allowed to rotate on the axis indicated with II in FIG. 1. Further rotation of the trocar 6 is provided by the joint assembly. More specifically, in the moving position, the cone 32 and the opening 31 extend at a mutual distance, allowing rotation of the U-shaped body 11 with respect to the connector 4 on the axis indicated with III in FIG. 1.

By pulling cable 5 in a direction indicated with I in FIG. 2b, clamp 1 is moved to its locking position. This movement urges the legs and therewith the clamping shoes 21 together, as indicated with the arrows, thereby clamping the instrument there between. Due to this clamping action, movement, i.e. rotation and translation, between the clamping shoes 21 and the instrument 7 is prevented. Further, due to the movement of the U-shaped body 11 in the direction I by pulling the cable 5, the opening 31 is urged onto the cone 32. The cone 32 and the opening 31 are then in frictional engagement, preventing movement between the cone 32 and the opening 31. Therefore, by pulling the cable 5, both the clamp member 2 and the joint assembly 3 are moved towards the locking positions.

The U-shaped body is manufactured from a resilient material, in this case plastic. The U-shaped body 11 is hereby pre-stressed towards the position as shown in 2a. Therefore, when the tension is released from the cable 5, the legs tend to move apart, thereby automatically moving the clamp 1 to the moving position.

In FIG. 3 an alternative of the clamp is shown. In this embodiment, the receiving member of the joint assembly 3 comprises two moveable walls 31a and 31b. The walls 31a and 31b are spaced apart to receive the cylinder 32 connected to the connector 4. Further, the clamping shoes 22a and 22b differ slightly from the clamping shoes from FIG. 1. The shoes 22a and 22b are connected to the legs of the body 11 using spindles 25, which are received in openings provided in the legs. This allows rotation of the shoes 22a and 22b with respect to the body 11 in the moving position on axis II. The legs of the body 11 are further provided with an opening for receiving the conical shaped connection sections 24 of the shoes 22a and 22b as shown in FIGS. 4a and 4b. The connection sections 24 extending in the openings in the legs, together forming a joint assembly, may however allow the rotation of the shoes with respect to the legs, without the use of spindles 25.

Also shown in FIG. 3 is a seal in the form of a tubular sleeve 64 made from silicones. The sleeve 64 provides an airtight environment in the trocar 6. The sleeve 64 is provided with openings to receive the clamping shoes 22a and 22b. These openings are smaller than the openings provided in the tube 61. As shown in more detail in FIG. 4b, the clamping shoes 22a and 22b are provided with a clamping section and a connecting section 24. Between the clamping section and the connecting section 24, the sleeve 64 can be received, providing an airtight connection.

Before use, the shoes 22a and 22b can be attached to the trocar 6 provided with the seal 64 to get the combination as shown in FIG. 4b. The seal 64 hereby functions to hold the shoes 22a and 22b and allows the shoes to move to and from the instrument 7. The shoes 22a and 22b can then be connected to the legs of the body 11, for instance using spindles 25.

The actuator 5 is furthermore arranged to apply a pulling force in a direction indicated with I which is out of the plane of the U-shaped body 11. When the cable 5 is pulled, the shoes 22a and 22b are moved together, as shown in FIG. 4a. This prevents movement of the instrument 7 in its longitudinal direction. The clamping action of the body 11 on the clamping shoes 22a and 22b furthermore prevents the shoes 22a and 22b to rotate with respect to the body 11. The conical shaped connection sections 24 and the complementarily formed openings in the body 11 increase the friction between the shoes 22a, 22b and the body 11.

Further, the walls 31a and 31b are moved together, clamping the cylinder 32. By pulling the cable 5, both the movement between the connector 4 and the body 11 and the movement between the body 11 and the instrument 7 is prevented. Similar to device as shown in FIG. 1, release of the tension on cable 5 moves the body 11 to the moving position due to the resilient material of the body 11, in this case stainless steel.

The clamping action of the shoes 22a and 22b are shown in more detail in FIG. 4a. The shoes 22a and 22b are provided with clamping surfaces which are arranged to engage a part of the perimeter of the instrument 7. Air flow is hereby allowed between the instrument 7 and the tube 61 of the trocar 6.

In FIG. 5a a trocar 6 is shown with an integrated clamping member in the form of clamping shoes 23a. Clamping shoes 23a and 23b (not visible in FIG. 5a) can be connected to the body 11 using spindles 25. To allow movement of the shoes 23a with respect to the tube 61 of the trocar 6, the tube 61 is provided with flexible wall sections 65a and 65b. Flexible sections 65a and 65b are formed by providing an incision in the wall of the tube 61. Sections 65a and 65b are then allowed to move with respect to an intermediate section 66. The incision for forming the flexible sections 65a and 65b is a small reduction in wall thickness. It can however also be possible to provide cuts opening in both the inner and the outer surface of the tube. A seal must then be provided to ensure an airtight system.

In FIG. 6a a second embodiment of a holding device 1 according to the invention is shown, wherein the holding body in the form of a sphere 11 is formed integral with the trocar 6. The sphere 11 comprises a plurality of segments 12 extending radially around the tube 61 of the trocar 6. The sections 12 of the sphere 11 allow the sphere 11 to be deformed. The sphere 11 is manufactured from a resilient material, in this case plastic.

In the embodiment shown in FIG. 6a, the protruding member of the joint assembly 3 is formed by the outer surface 32 of the sphere 11. This outer surface 32 is received by the receiving member in the form of ring 31, which is complementarily to the outer surface 32. The ring 11 is open at one end forming ends 31a and 31b, wherein end 31a is provided with a connector 4. Between said ends 31a and 31b extends the actuator in the form of hydraulic piston-cylinder combination 53. The hydraulic actuator 53 is in this case arranged to be connected to a luer lock. When hydraulic pressure, e.g. by means of a physiological saline solution, is supplied to the hydraulic actuator 53, the ends 31a and 31b are urged apart, changing the diameter of the ring 31. The actuator is further provided with a spring 52, biasing the ends 31a and 31b together.

To operate the actuator 53, a manipulator in the form of a knob is provided (not shown). The knob is provided on a distance from the actuator 53 and the holding device 1. More specifically, the knob is provided on the instrument 7 allowing the surgeon to operate the knob while handling the instrument 7. The knob is in this case arranged to supply hydraulic pressure to the hydraulic actuator 53. When the knob is operated, the ends 31a and 31b are urged apart.

When the joint assembly 3 is in the moving position, as will be explained more in detail below, the sphere 11 with its outer surface 32 is allowed to rotate in ring 31, as is shown in FIG. 6b. It will be appreciated that this joint assembly 3 allows a flexible movement of the trocar 6 with respect to the connector 4.

The sphere 11 is furthermore provided with a channel which extends coaxially with the tube 61. The instrument 7 can therefore be held in the tube 61 and the channel in the sphere 11, as can be seen in FIGS. 7a and 7b. The inner surface or wall 26 of the sphere 11 hereby forms the clamping member according to the invention.

In FIG. 7a the sphere 11 is in the moving position due to the supply of hydraulic fluid to the hydraulic piston 53. The ends 31a and 31b are urged apart and this allows the sphere 11 to expand, since the sphere 11 is pre-stressed into the moving position. In this position, the sections 12 of the sphere 11 extend at a distance from each other. The diameter of the wall 26 is therefore larger than the outer surface of the instrument 7, allowing movement between the instrument 7 and the sphere 11. The clamp member is now in the moving position.

Since the distance between the ends 31a and 31b is larger, the sphere 11, more specifically the outer surface 32 thereof, and the ring 31 are also allowed to move with respect to each other, allowing rotation of the tube 61 as is indicated in FIG. 6b.

When the pressure in the hydraulic cylinder 53 is released by releasing the knob, the spring 52 will urge the ends 31a and 31b together, as can be seen in FIG. 7b. The ring 31 hereby deforms the sphere 11 and the sections 12 now abut each other. The ring 31 now frictionally engages the outer surface 32 of the sphere 11, limiting movement therebetween. Further, due to the deformation, the segments 12 are urged radially inwards with respect to the longitudinal axis of the instrument 7, clamping said instrument 7. The diameter of the clamping member in the form of wall 26 is thereby decreased, preventing movement of the instrument 7 with respect to the sphere 11.

When the ends 31a and 31b are moved together due to the spring 52, both the joint assembly 3 in the form of the ring 31 and the sphere 11 and the clamp member in the form of the inner surface 26 are moved to the locking position.

Figure 8B:
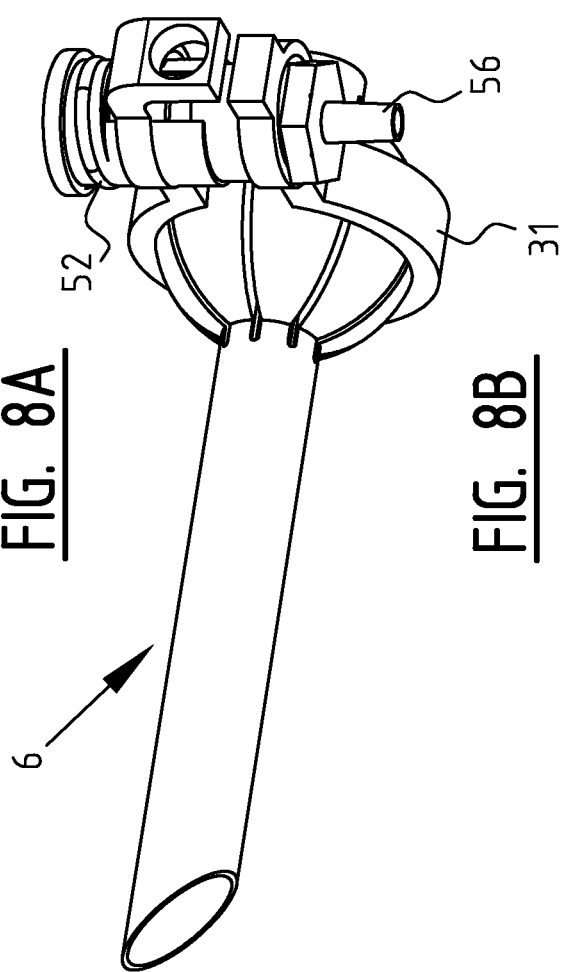

In FIG. 8a a variant is shown, wherein the actuator comprises a nut 55. Turning the nut 55 will urge the ends 31a and 31b together, moving the sphere 11 to the locking position. In FIG. 8b, the actuator is connectable to a Bowden cable, wherein pulling the cable moves the ends 31a and 31b together.

The present invention is not limited to the embodiment shown, but extends also to other embodiments falling within the scope of the appended claims. It should for instance be noted that various parts of particular shown embodiments can be used in other embodiments. It is for instance possible to exchange the different clamping shoes, the U-shaped bodies and the actuators between the variants shown in FIGS. 1 to 5. The clamping shoes shown in FIGS. 4a and 4b are however preferred. It is furthermore possible to use other forms than rings for the receiving member in the embodiments shown in FIGS. 6 to 8. The ring can for instance be U-shaped, wherein the sphere is clamped between the legs. It should further be noted that although a distance between the clamp member and the instrument 7 is shown in the moving position in FIGS. 4b and 7a, it is in practice preferable to have contact between the clamp member and the instrument 7 in the moving position, albeit no firm clamping contact. This prevents any lateral movement of the instrument with respect to the trocar. Further, although a knob as manipulator in combination with the embodiment of FIG. 6a is described, also the other embodiments are provided with a suitable manipulator provided on the instrument for easy access for the surgeon. The manipulator is further not limited to a knob. For instance, in case a Bowden cable is used, the manipulator may comprise a suitable handle for pulling said cable.

The invention claimed is:

1. A holding device for holding a manually operated medical device in place, comprising:
    a connector arranged to connect the holding device to a positioning apparatus;
    a clamp member arranged to clamp the medical device, wherein the clamp member is moveable between a locking position, wherein the medical device is clamped and a moving position, wherein the medical device is moveable with respect to the holding device;
    a guiding tube for receiving the medical device, wherein a part of a wall of the guiding tube is arranged to receive the clamp member for clamping the guiding tube and the medical device in the guiding tube;
    a holding body, wherein the holding body is formed integrally with the guiding tube, and comprises a channel having an inner wall and an outer wall, wherein the inner wall of the channel forms at least a part of an inner wall of the guiding tube;
    a joint assembly arranged to allow movement between the clamp member and the connector, wherein the joint assembly is moveable between a moving position, wherein the clamp member is moveable with respect to the connector and a locking position, wherein movement between the clamp member and the connector is prevented, and;
    an actuator for moving both the joint assembly and the clamp member between the moving position and the locking position.

2. The holding device according to claim 1, wherein at least one of the clamp member and the joint assembly is arranged to move between the positions due to movement of the other one of the joint assembly and the clamp member between the positions.

3. The holding device according to claim 1, wherein the actuator is arranged to move the holding body between a moving position and a locking position for moving the clamp member and the joint assembly between the moving position and the locking position, wherein the holding body is at least partially manufactured from a resilient material, and wherein the holding body is pre-stressed towards the moving position or the locking position of the holding body.

4. The holding device according to claim 3, wherein the holding body is substantially U-shaped and comprises two legs, wherein the two legs of said U-shaped holding body form the clamp members for clamping the medical device there between.

5. The holding device according to claim 4, wherein the clamping member is rotatable on the holding body.

6. The holding device according to claim 4, wherein the clamp member is arranged to clamp the medical device in the guiding tube, wherein the guiding tube comprises a trocar adapted for use with the holding device.

7. The holding device according to claim 1, wherein the actuator comprises a manipulator configured to allow a surgeon to operate the actuator, wherein the manipulator extends at a distance from the actuator.

8. The holding device according to claim 1, wherein the joint assembly comprises a protruding member and a receiving member for receiving the protruding member, wherein the receiving member is substantially complementary to the protruding member, wherein the actuator is arranged to induce movement between the receiving member and the protruding member for moving between the locking position and the moving position.

9. The holding device according to claim 8, wherein the protruding member has a substantially cylindrical, conical or spherical shape.

10. The holding device according to claim 8, wherein the actuator is arranged to modify a diameter of the receiving member of the joint assembly for deforming the holding body for moving both the joint assembly and the clamp member between a locking position and a moving position.

11. The holding device according to claim 8, wherein the receiving member of the joint assembly is provided on a holding body, wherein the actuator is arranged to modify the shape of the receiving member.

12. The holding device according to claim 1, wherein the holding body comprises a channel for receiving the medical device, wherein an inner surface of said channel forms said clamp member, wherein an outer surface of the holding body forms a protruding member of the joint assembly, and wherein the actuator is arranged to deform the holding body for moving the holding body between the moving position and the locking position.

13. The holding device according to claim 12, wherein the holding body comprises a plurality of segments extending radially from said channel.

14. The holding device according to claim 1, wherein the guiding tube is provided with at least one opening for receiving the clamp member.

15. The holding device according to claim 1, wherein the guiding tube is provided with a moveable wall for cooperation with the clamp member.

16. The holding device according to claim 1, wherein the inner wall of said guiding tube is moveable for clamping said medical device.

17. The holding device according to claim 1, wherein the guiding tube is a trocar.

18. The holding device according to claim 1, wherein the holding body is in the form of a sphere and wherein the sphere comprises a plurality of segments extending radially around the guiding tube.

* * * * *